United States Patent
Mielekamp

(10) Patent No.: US 8,232,992 B2
(45) Date of Patent: Jul. 31, 2012

(54) IMAGE PROCESSING SYSTEM AND METHOD FOR SILHOUETTE RENDERING AND DISPLAY OF IMAGES DURING INTERVENTIONAL PROCEDURES

(75) Inventor: Pieter Maria Mielekamp, Veldhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 761 days.

(21) Appl. No.: 12/092,436

(22) PCT Filed: Oct. 25, 2006

(86) PCT No.: PCT/IB2006/053925
§ 371 (c)(1),
(2), (4) Date: May 2, 2008

(87) PCT Pub. No.: WO2007/052184
PCT Pub. Date: May 10, 2007

(65) Prior Publication Data
US 2008/0278489 A1 Nov. 13, 2008

(30) Foreign Application Priority Data
Nov. 2, 2005 (EP) .................................... 05110272

(51) Int. Cl.
*G06T 17/00* (2006.01)
(52) U.S. Cl. .................... 345/424; 382/266; 382/295
(58) Field of Classification Search ................... None
See application file for complete search history.

(56) References Cited

U.S. PATENT DOCUMENTS

| | | | |
|---|---|---|---|
| 6,083,162 A * | 7/2000 | Vining | 600/407 |
| 6,166,742 A * | 12/2000 | He | 345/421 |
| 6,297,799 B1 | 10/2001 | Knittel et al. | |
| 6,301,498 B1 | 10/2001 | Greenberg et al. | |
| 6,343,936 B1 | 2/2002 | Kaufman et al. | |
| 6,842,638 B1 | 1/2005 | Suri et al. | |
| 7,327,365 B2 * | 2/2008 | Chen et al. | 345/426 |
| 2002/0138974 A1* | 10/2002 | Suhara et al. | 29/740 |
| 2003/0181809 A1* | 9/2003 | Hall et al. | 600/425 |
| 2005/0015006 A1 | 1/2005 | Mitschke et al. | |
| 2005/0074157 A1 | 4/2005 | Thomas, III | |

(Continued)

FOREIGN PATENT DOCUMENTS
WO WO9816903 A1 4/1998
(Continued)

OTHER PUBLICATIONS

Nagy et al: "High-Quality Silhouette Illustration for Texture-Based Volume Rendering"; Journal of WSCG, vol. 12, No. 1-3, 8 Pages, Feb. 2004.

(Continued)

*Primary Examiner* — Kee M Tung
*Assistant Examiner* — Michelle Chin

(57) ABSTRACT

A medical viewing system in which 3DRA images of a body volume are acquired and two dimensional live image data is acquired within the body volume during an intervention. Direct volume silhouette rendering is performed in respect of the 3D image so as to generate a silhouette rendering of the 3D image comprised of values proportional to the translucency of voxels of the 3D image data, and the live sequence of 2D images (18) is displayed within the resultant silhouette rendering of the body volume. A user can control the levels of shading and/or contrast in the displayed silhouette rendering.

19 Claims, 4 Drawing Sheets

U.S. PATENT DOCUMENTS

2007/0146389 A1* 6/2007 Distler .................. 345/629
2008/0165141 A1* 7/2008 Christie ................ 345/173

FOREIGN PATENT DOCUMENTS

| WO | WO9960921 | A1 | 12/1999 |
| WO | WO2004034329 | A2 | 4/2004 |
| WO | WO2004044847 | A1 | 5/2004 |

OTHER PUBLICATIONS

Levoy, M.: "Display of Surfaces From Volume Data"; IEEE Computer Graphics and Applications, vol. 8, No. 3, May 1998, pp. 29-37.
Fuchs et al: "Interactive Visualization of 3D Medical Data"; Computer, vol. 22, No. 8, Aug. 1989, pp. 46-51.

* cited by examiner

IMAGE PROCESSING SYSTEM AND METHOD FOR SILHOUETTE RENDERING AND DISPLAY OF IMAGES DURING INTERVENTIONAL PROCEDURES

The invention relates generally to an image processing system and method for enabling visualisation and investigation of internal parts of a live subject by acquiring live, two-dimensional images in respect thereof during an interventional procedure, and displaying the live, two-dimensional images relative to three-dimensional volume data.

The imaging of body volumes and internal parts of a live subject is practiced notably in the field of medical diagnostics and therapy, that is, in the context of X-ray fluoroscopy. Therefore, the X-ray projection of a biological body volume will be considered hereinafter by way of example, but the present invention is not intended to be restricted thereto and can be used in all fields of application with similar secondary conditions.

Referring to FIGS. 1 and 2 of the drawings, a typical X-ray system comprises a swing arm (C-arc or G-arc) 1 supported proximal a patient table 2 by a robotic arm 3. Housed within the swing arm 1, there is provided an X-ray tube 4 and an X-ray detector 5, the X-ray detector 5 being arranged and configured to receive X-rays 6 which have passed through a patient 7 and generate an electrical signal representative of the intensity distribution thereof. By moving the swing arm 1, the X-ray tube 4 and detector 5 can be placed at any desired location and orientation relative to the patient 7.

In the treatment of various types of condition and disease, a special medical application is provided by the fluoroscopic observation of the propagation of a catheter in the vascular system of the patient. Thus, during intervention, a catheter or guidewire is required to be advanced and/or a stent or coil is required to be introduced under X-ray surveillance (fluoroscopy), and as accurately as possible, through the vessels to an internal part of interest. While this procedure is performed, the vessel structures are made visible on a first monitor for short periods of time, in the form of two-dimensional live images, by introducing short bursts of a radio-opaque contrast agent through the catheter and obtaining X-ray images using, for example, the system described with reference to FIGS. 1 and 2 of the drawings.

For the safety of the patient, it is highly desirable to minimise the exposure to X-rays and also to minimise the amount of contrast agent introduced into the body, and it is therefore known to display during an intervention, on a second monitor, one or more pre-interventional X-ray images acquired in respect of the area of interest, so as to assist navigation. These pre-interventional images support the orientation for the attendant physician as a "vascular map" or "road map" of the vascular system. In order to improve guidance during, for example, catheter placement, methods have been developed to overlay such roadmap information on the fluoroscopic images obtained during the intervention, as described in, for example, WO2004/034329.

However, it is highly desirable for the physician to be able to visualise in three dimensions, the two-dimensional fluoroscopic image data acquired during an intervention, as this will enable interventional data to be tracked in real time, whilst significantly reducing the contrast fluid and X-ray exposure load on the patient during the interventional procedure. The three-dimensional image data may, for example, be acquired by means of a 3D rotational scan (optionally wherein a contrast agent is injected into the body volume to be imaged), which may be particularly advantageous since such a scan (e.g. 3D rotational angiography or 3DRA) is routinely obtained prior to any intervention for diagnostic and treatment evaluation purposes.

Silhouette renderings are useful to effectively convey a great deal of information, such as the structure of a volume model, with a few strokes (see FIG. 3b, which is a silhouette rendering of an aneurysm, compared with the surface rendering thereof shown in FIG. 3a). Silhouette rendering algorithms can be divided into two sub-classes:

1. Based on polygonal representations (surface rendering)
2. Tailored to volume voxel representations (direct volume rendering)

As will be known to a person skilled in the art, for polygonal meshes, the silhouette edges consist of visible segments of all edges that connect back-facing polygons to front-facing polygons and very effective silhouette rendering algorithms for polygonal based representations exist in terms of speed and robustness. However, there are a number of drawbacks associated with polygonal-based, surface rendering techniques, including the significant pre-processing overhead and the vast amount of memory needed for vessel segmentation (whereby the venous signal is reduced or eliminated) and iso-surface generation/representation. In the context of vessel segmentation for 3DRA volumes, the existence of bone or other opaque material makes automatic vessel segmentation difficult. Here, such segmentation would usually need some user-interaction for fine-tuning, which is rather cumbersome given the significant pre-processing overhead. Furthermore, the explicit segmentation may lead to differences (loss of small vessels) between surface and volume representations.

The problems outlined above in relation to polygonal representations could, in theory, be overcome by using voxel representations instead. However, while various methods exist for voxel-based silhouette rendering, none of these methods can compete in terms of speed with the polygonal-based methods due, at least in part, to the fact that known voxel-based methods all use some form of explicit classification for detecting boundaries/contours, usually based on voxel discontinuities.

It is therefore an object of the present invention to provide an image processing system and method which enables silhouette rendering of three-dimensional representations of two-dimensional image data captured in respect of a body volume, which is fast enough to be used in respect of live two-dimensional image data, without the significant pre-processing overhead associated with conventional polygonal-based representations.

In accordance with the present invention, there is provided an image processing system for displaying an image of a body volume, the system comprising means for receiving three dimensional image data in respect of said body volume, silhouette rendering means for generating a direct volume silhouette rendering of said three dimensional image data, said silhouette rendering being comprised of values proportional to the translucency of voxels of said three dimensional image data, and means for displaying the resultant silhouette rendering.

Also in accordance with the present invention, there is provided a method of displaying an image of a body volume, comprising receiving three-dimensional image data in respect of said body volume, generating a direct volume silhouette rendering comprised of values proportional to the translucency of voxels of said three dimensional image data, and displaying the resultant silhouette rendering.

The present invention extends to a medical viewing system for displaying a sequence of medical images, the system comprising acquisition means for acquiring three dimensional image data in respect of a body volume, acquisition means for acquiring a sequence of two dimensional images within said body volume, image processing means as defined above, and means for displaying the sequence of two dimensional images within the displayed silhouette rendering of said three dimensional image data.

Because the voxel translucencies instead of the voxel densities are visualised during silhouette rendering, the brightness variation is reversed and the structures (e.g. vessels) in the body volume have maximum brightness at the contours and minimum brightness in the centre, and it is possible to implement additional, relatively fast two-dimensional image processing techniques in respect of the silhouette rendering for display with hardly any additional overhead. Thus, more specifically, the image processing means may comprise means for varying the levels of contrast and/or shading in the silhouette rendering for display. In a preferred embodiment, control means, beneficially analogue control means (e.g. slider control means) may be provided for enabling a user to select and control the levels of contrast and/or shading in the silhouette rendering for display. Edge enhance means may be provided to emphasise silhouette contrast, by means of, for example, an unsharp 3*3 convolution filter. Means may be provided to perform an intensity correction (e.g. inverse gamma) in respect of the silhouette rendering for display so as to enable the darkness level of structures in the body volume to be controlled while maintaining the brightness of the silhouettes.

The direct volume silhouette rendering performed by the silhouette rendering means may be implemented by, for example, ray-casting or by means of rendering textured slices through the volume of voxel densities in a back-to-front or front-to-back sorting order.

These and other aspects of the present invention will be apparent from, and elucidated with reference to, the embodiments described herein.

Embodiments of the present invention will now be described by way of examples only and with reference to the accompanying drawings, in which.

Prior to an intervention, a 3D rotational scan is acquired, reconstructed and prepared for visualisation. During the actual intervention, live 2D (fluoro) images are acquired, processed and visualised in combination with the 3D volumes. The 2D images may be visualised in combination with the 3D volumes substantially in real-time, during the intervention, or they may have been pre-processed and/or stored such that they can be reviewed and presented in combination with and relative to the volume data. Furthermore, live fluoro data may be continuously stored in a cyclic buffer that can be reviewed at any time (with the 3D-volume data), without being stored on a long-term storage medium.

As mentioned above, silhouette renderings are useful to effectively convey a great deal of information, such as the structure of a volume model, with a few strokes. By combining silhouettes to render the volume data with the live 2D data, a deal of the volume information can still be conveyed, while this rendering method provides minimal obstruction for the live data. As explained above, in relation to polygonal representations (surface rendering), effective silhouette rendering algorithms exist in terms of speed and robustness, but there are a number of disadvantages associated with this technique, which make it less suitable for use in visualisation of live 2D image data with 3D volume data.

Conventional texture-based silhouette rendering uses some form of iso-surface extraction based on the voxel opacity in order to explicitly extract the silhouettes.

Figure 1:
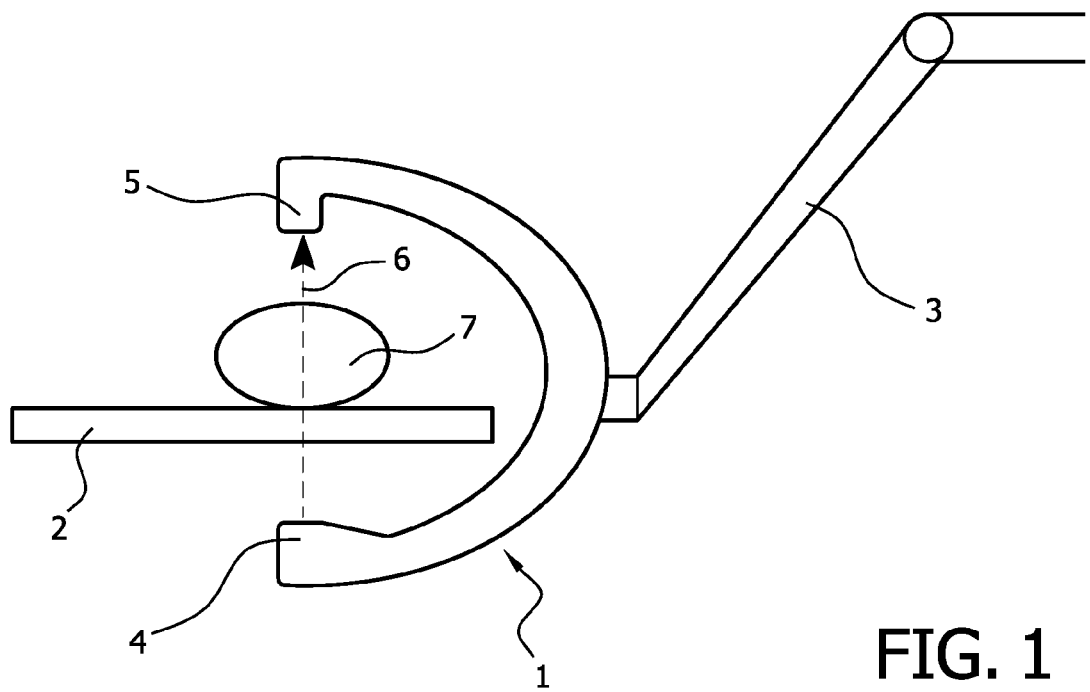
FIG. 1 is a schematic side view of an X-ray swing arm.
Figure 2:
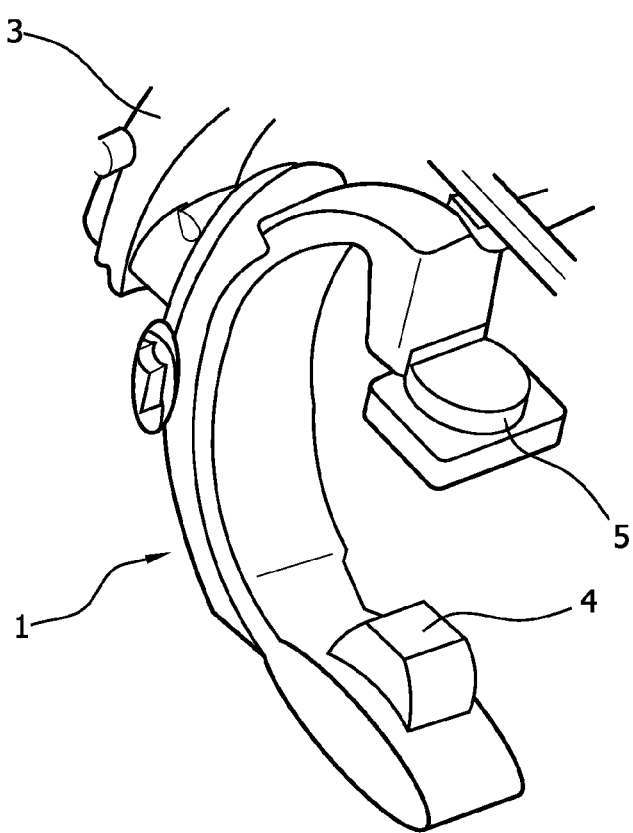
FIG. 2 is a perspective view of an X-ray swing arm.
Figure 3A:
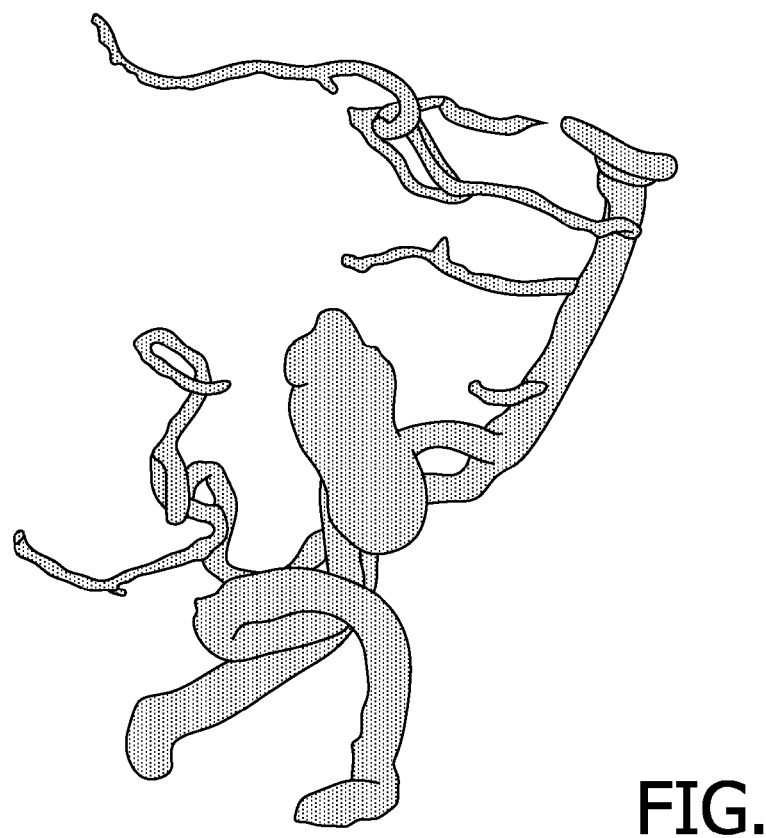
FIGS. 3a and 3b are respective surface and silhouette renderings of an aneurysm.
Figure 3B:
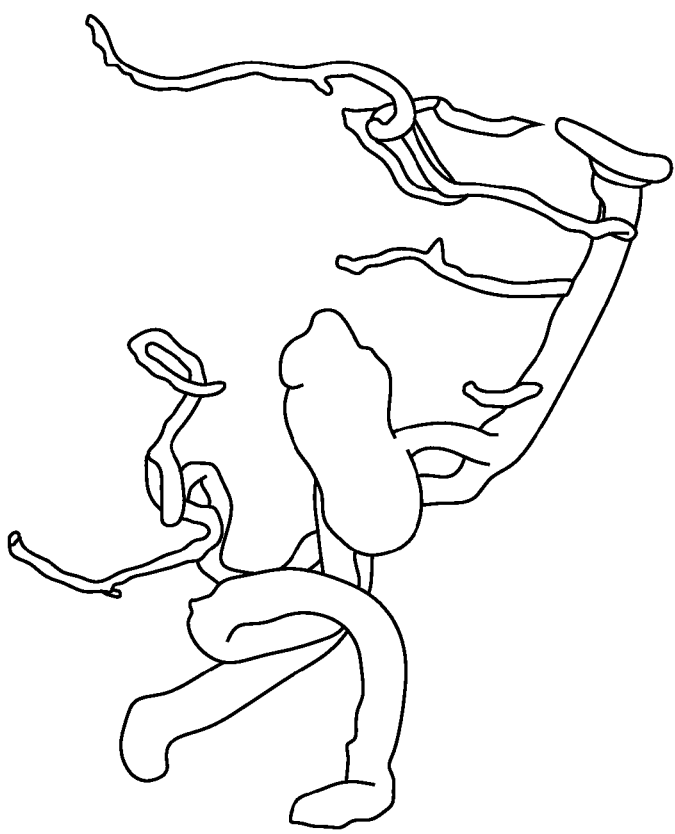
Figure 4:
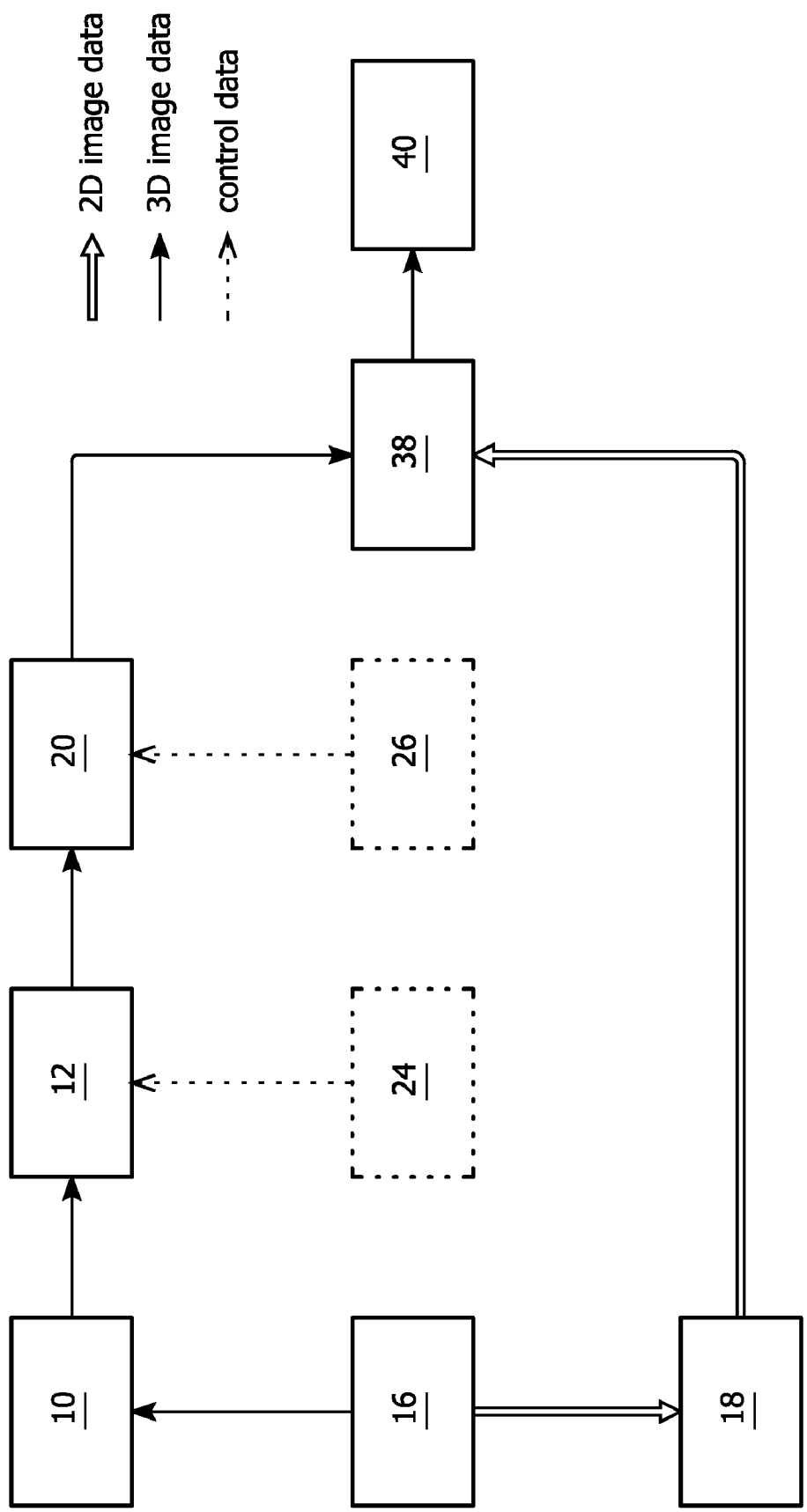
FIG. 4 is a schematic block diagram illustrating the principal features of an image display system according to an exemplary embodiment of the present invention.
Figure 5A:
FIG. 5 illustrates images A to D with varying degrees of 3D shading.
Figure 5B:
Figure 5C:
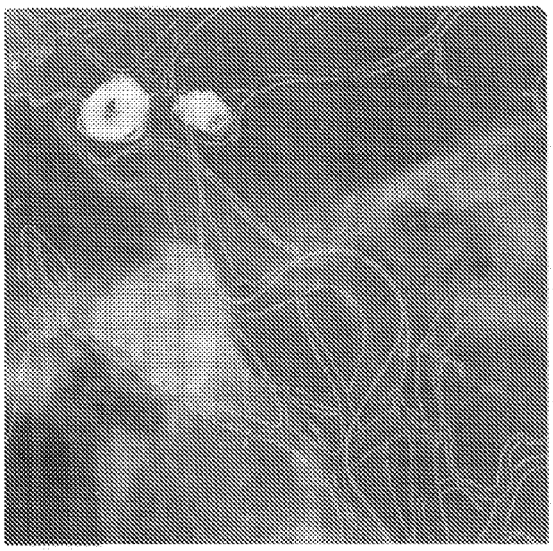
Figure 5D:
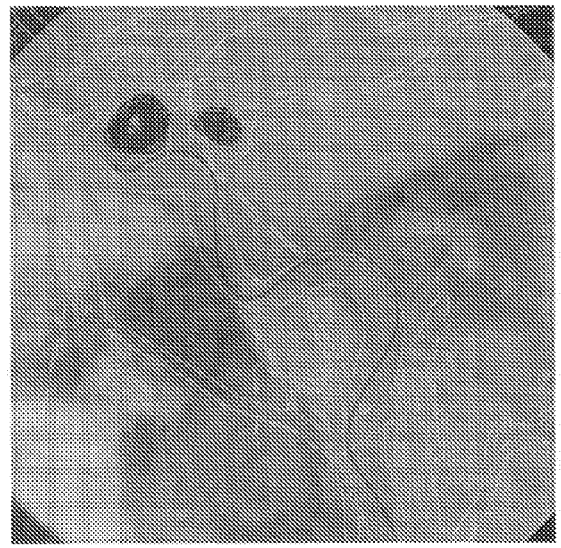

Referring to FIG. 4 of the drawings, there is illustrated, in schematic block diagram form, an image display system according to an exemplary embodiment of the present invention for the display of 3D Rotational Angiography roadmapping, where 2D live images are displayed together with 3D reconstructional vessel information. The illustrated system comprises means 10 for receiving three-dimensional image data representative of a body volume, which image data is acquired by, for example, a 3 DRA (rotational angiography) technique. This image data is reconstructed at module 12. Means 16 are also provided for receiving live, two-dimensional image data in respect of the body volume acquired, for example, by means of X-ray fluoroscopy techniques as a surgical instrument is moved through the body volume. The live images produced (denoted at block 18) are fed to an image composition module 38 and displayed at module 40. A window width/level range selection module 24 renders the translucency of the body volume in respect of which 3D images are acquired by the means 10, as will be described in more detail later, and the resultant control data is fed to the 3D volume visualisation module 12. By means of the 2D image processing module 20 (executed on the Graphical Processing Unit or GPU) more emphasis can be put on the silhouettes whilst the insides of the vessels are darkened, and the resultant images A-D can be generated, as shown in FIG. 5 of the drawings. By means of a silhouette (slider) control module 26, the user is able to gradually go through the images displayed on module 40 from A to D, thereby controlling the desirable amount of 3D shading.

In a known texture-based silhouette rendering method, an algorithm is used that takes the regular volumetric dataset as input, without any additional information, such as gradients. The rendering of the dataset is accomplished by using 3D texturing under the constraint of slicing the polygons in front-to-back fashion using iso-surface extraction. In such known Direct Volume renderings of 3DRA volumes, the resultant values represent the radio opaque voxel densities, wherein the vessels have their maximum brightness in the centre and minimum brightness at the contours. In accordance with the invention, however, the voxel translucencies are visualised (using normal window width/level range selection at module 24 in FIG. 4), instead of voxel densities, such that this brightness variation is reversed and the vessels have maximum brightness at the contours. In order to emphasise the silhouette contrast, edge enhancement may be applied by means of a known unsharp masking 3*3 convolution filter. Finally, to control the darkness level of the vessels, while keeping the brightness of the silhouettes, an intensity correction (e.g. inverse gamma) may be applied. By controlling the filter kernel and the intensity correction (at control module 26 in FIG. 4), the desired level of 2D/3D contrast/shading in the image displayed in the display means 40 can be selected and controlled by a user. By using known graphics hardware, the additional 2D image processing proposed by the present invention can be implemented very fast with hardly any additional overhead.

As described above, in the present invention, the voxel translucencies are visualised instead of voxel densities, and this may be achieved by a small modification to a known Direct Volume rendering algorithm, such as that described by Zoltan Nagy and Reinhard Klein in "High-Quality Silhouette Illustration for Texture-Based Volume Rendering", Journal of WSCG, Vol. 12, No. 1-3, ISSN 1213-6972, and as will be apparent to a person skilled in the art. The resultant volume rendering equation can be implemented by ray-casting or by means of rendering textured slices through the volume of voxel densities in a back-to-front or front-to-back sorting order using, for example, the following algorithms:

BackToFront Renderer:
Foreach (slice,s, from back to front)
    colour=s.opacity*s.colour+(1−s.opacity)*colour
FrontToBack Rendered
colour=0
opacity=0
Foreach (slice,s, from front to back)
    colour=colour+(1−s.opacity)*s.opacity*s.colour
    opacity=opacity+(1−opacity).s.opacity
    In both algorithms the colour is pre-multiplied by the opacity of the voxels;
where s.colour=s.col*s.opacity
Now by pre-multiplying with the voxel translucency
where s.colour=s.col*(1−s.opacity)
the volumes translucency can be rendered.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A medical diagnostic image processing system for displaying an image of a body volume of a living subject including blood vessels, the system comprising:
    a source of a series of two-dimensional projection images of the body volume generated as a catheter moves through the blood vessels;
    a processor configured to:
        receive three dimensional image data of said body volume,
        render a direct volume silhouette image from said three dimensional image data, said volume silhouette image being rendered with voxel values proportional to a translucency of voxels of said three dimensional image data,
        apply an edge enhancement filter to emphasize edges of the blood vessels in the volume silhouette image,
        register and sequentially combine each of the series of two dimensional projection images on the volume silhouette image to show the catheter moving through the edge enhanced blood vessels,
        vary levels of contrast and/or shading in the displayed volume silhouette image to adjust the translucency of the voxels;
    a display which displays the registered and combined resultant volume silhouette image combined with each of the series of two-dimensional projection images; and
    a user control by which a user selects and controls the level of contrast and/or shading in the volume silhouette image for display.

2. The system according to claim 1, wherein said user control comprises an analogue control.

3. The system according to claim 1, wherein the direct volume silhouette image is rendered by rendering textured slices through the volume of voxel densities in a back-to-front or front-to-back sorting order.

4. The system according to claim 1, further including:
    an edge enhancement user control by which the user controls a degree of edge enhancement of the blood vessels in the volume silhouette image.

5. The system according to claim 4, wherein edges of the blood vessels are enhanced by brightening the edges and wherein said processor is further programmed to:
    perform an intensity correction to the displayed volume silhouette image which controls a darkness level of structures in the body volume while maintaining a brightness of the silhouette edges of the blood vessels.

6. The system according to claim 1, wherein direct volume silhouette image is rendered by ray-casting.

7. The image processing system according to claim 1, wherein the source of two dimensional images includes an X-ray fluoroscope.

8. The image processing system according to claim 1, wherein the contours are enhanced by maximizing a brightness of the edges of the vessels relative to non-edge portions of the volume silhouette image.

9. The system according to claim 1, wherein rendering the silhouette image includes segmenting the blood vessels with a polygonal mesh and the silhouette edges consist of visible segments of all polygon edges that connect back-facing and front-facing polygons.

10. A method of tracking a catheter by displaying images of a body volume of a living subject which includes vasculature as a catheter moves through the vasculature, the method comprising:
    receiving three-dimensional image data of said body volume;
    generating a direct volume silhouette image from the three-dimensional image data in which image voxels each have an adjustable translucency and in which edges of the vasculature are brightness enhanced to be brighter than other voxels interior to the volume silhouette image;
    receiving a sequence of two-dimensional images of said body volume as the catheter moves through the vasculature;
    combining each received two dimensional image of the sequence of two dimensional images with the volume silhouette image to generate a series of combination images in which the catheter is displayed within the bright edges of the vasculature; and
    displaying the series of combination images depicting movement of the catheter in the vasculature.

11. The method according to claim 10, further comprising:
    with a user operated control, adjusting the translucency of the volume silhouette image in the series of combination images.

12. The method according to claim 11 further including:
    with a user operated control, adjusting the translucency of the volume silhouette image.

13. The method according to claim 10 further including:
enhancing a brightness of the edges of the vasculature to brighten the edges relative to non-edge portions of the vasculature.

14. The method according to claim 13 further including:
with a user operated control, controlling application of an edge enhancement filter to control contrast between the volume silhouette image relative to the brightness of the brightness enhanced edges of the vasculature.

15. A medical viewing system for displaying a sequence of medical images depicting movement of a device through anatomical structure of a living subject, the system comprising:
a source of three dimensional image data of a body volume of the living subject, the three dimensional image data for reconstruction into a volume image composed of voxels, a value of each voxel depicting density of a corresponding voxel of the body volume;
a sources of sequentially generated two-dimensional images of the body volume as the device moves through the anatomical structure of the living subject;
one or more processors programmed to:
process the three dimensional image data to generate a volume silhouette rendering which has a controllable translucency,
enhance edges of the anatomical structure in the volume silhouette rendering such that the edges are brighter than non-edges in the volume silhouette rendering,
sequentially combine each of the two dimensional images with the volume silhouette rendering to generate a sequence of combination images depicting the body volume of the living subject as the device moves through the anatomical structure of the living subject;
a display device which displays the sequence of combination images; and
a user operated control by which a user adjusts the transparency of the volume silhouette rendering.

16. The system according to claim 15 wherein the user control is configured to enable the user to adjust at least one of contrast and shading in the sequence of combination images.

17. The system according to claim 15 wherein user control is further configured to enable the user to adjust darkness levels of the volume silhouette rendering while maintaining brightness of the edges.

18. The system according to claim 17 wherein the volume silhouette rendering represents a tubular anatomical structure in the body volume and the series of two dimensional images depict the device moving through the vasculature.

19. The system according to claim 18 wherein the source of the two dimensional images includes a C-arm x-ray scanner which provides a fluoroscopic data depicting propagation of a catheter moving through vasculature of the living subject, edges of the vasculature being brightness enhanced.

* * * * *